(12) United States Patent
Kalakodimi et al.

(10) Patent No.: US 10,407,778 B2
(45) Date of Patent: Sep. 10, 2019

(54) CORROSION INHIBITION FOR AQUEOUS SYSTEMS USING A HALOGENATED TRIAZOLE

(71) Applicant: CHEMTREAT, INC., Glen Allen, VA (US)

(72) Inventors: Prasad Kalakodimi, Glen Allen, VA (US); Raymond Post, Glen Allen, VA (US); Caibin Xiao, Hopkinton, MA (US); Dale Stuart, Glen Allen, VA (US)

(73) Assignee: CHEMTREAT, INC, Glen Allen, VA (US)

(*) Notice: Subject to any disclaimer, the term of this patent is extended or adjusted under 35 U.S.C. 154(b) by 155 days.

(21) Appl. No.: 15/618,921

(22) Filed: Jun. 9, 2017

(65) Prior Publication Data
US 2017/0356093 A1    Dec. 14, 2017

Related U.S. Application Data

(60) Provisional application No. 62/347,976, filed on Jun. 9, 2016.

(51) Int. Cl.
C23F 11/00 (2006.01)
C23F 11/14 (2006.01)
(Continued)

(52) U.S. Cl.
CPC .......... *C23F 11/146* (2013.01); *C23F 11/149* (2013.01); *G01N 21/643* (2013.01);
(Continued)

(58) Field of Classification Search
CPC .... C23F 11/146; C23F 11/149; G01N 21/643; G01N 21/645
See application file for complete search history.

(56) References Cited

U.S. PATENT DOCUMENTS 2,618,606 A    11/1952    Schaeffer
2,643,177 A    6/1953    Wachter et al.
(Continued)

OTHER PUBLICATIONS

International Searching Authority, Notification of Transmittal of the International Search Report and Written Opinion of the International Searching Authority, or the Declaration, dated Sep. 1, 2017, pp. 10.
(Continued)

*Primary Examiner* — Sean E Conley
(74) *Attorney, Agent, or Firm* — Oliff PLC

(57) ABSTRACT

A method for inhibiting corrosion of a corrodible metal surface that contacts water in a water system is provided. The method may include introducing into the water a treatment composition including an ex-situ halogenated triazole compound in an amount sufficient for inhibiting corrosion. A method of measuring a concentration of the ex-situ halogenated triazole compound in water in a water system is also provided. The method may include inducing the halogenated triazole compound to fluoresce and measuring an intensity of the fluorescence emitted from the water to determine the concentration of the halogenated triazole compound in the water. The concentration of the halogenated triazole can be monitored and controlled. The concentration of the halogenated triazole can be adjusted to a desired level based on the measured fluorescence value.

16 Claims, 11 Drawing Sheets

(51) Int. Cl.
  *G01N 21/64*   (2006.01)
  *G01N 21/85*   (2006.01)
  *G01N 33/18*   (2006.01)
  *G01N 17/00*   (2006.01)

(52) U.S. Cl.
  CPC ........... *G01N 21/645* (2013.01); *G01N 21/85* (2013.01); *G01N 17/006* (2013.01); *G01N 33/18* (2013.01); *G01N 2021/6439* (2013.01)

(56) References Cited

U.S. PATENT DOCUMENTS

| | | |
|---|---|---|
| 2,877,188 A | 3/1959 | Liddell |
| 3,295,917 A | 1/1967 | Cotton et al. |
| 5,278,074 A | 1/1994 | Rao et al. |
| 5,411,677 A | 5/1995 | Pickering et al. |
| 5,863,464 A | 1/1999 | Reichgott et al. |
| 5,874,026 A | 2/1999 | Pilsits, Jr. et al. |
| 5,968,408 A | 10/1999 | Anderson et al. |
| 6,376,065 B1 | 4/2002 | Korba et al. |
| 2003/0035749 A1 | 2/2003 | Hann et al. |
| 2015/0152329 A1 | 6/2015 | Seetharaman et al. |

OTHER PUBLICATIONS

Hollander et al., "The Chemistry of Azole Copper Corrosion Inhibitors in Cooling Waters," Corrosion, vol. 41, No. 1, Jan. 1985 (Abstract).

CORROSION INHIBITION FOR AQUEOUS SYSTEMS USING A HALOGENATED TRIAZOLE

TECHNICAL FIELD

This disclosure relates generally to inhibiting corrosion of metal surfaces in contact with water in a water system by introducing an ex-situ halogenated triazole compound into the water, and measuring, monitoring, and controlling an amount of the halogenated triazole compound in the water based on the fluorescence intensity of the water.

BACKGROUND

Corrosion of metals and metallic surfaces in aqueous environments, such as water systems, is a significant problem, estimated by the National Association of Corrosion Engineers to cost approximately 3% of U.S. GDP. Corrosion inhibitors are commonly applied to aqueous systems to reduce corrosion damage. Precise dosing and control of corrosion inhibitors is required to achieve optimum performance.

Triazole compounds can be used to inhibit the corrosion of metals, such as copper, steel, and galvanized metal, in aqueous and non-aqueous environments. To function effectively in aqueous systems, the water contacting a metal surface must contain an appropriate concentration of the corrosion inhibitor. Maintaining the proper dosage can be problematic for several reasons. Industrial systems have water losses, either intentionally or due to leakage. The corrosion inhibitor must be replenished to account for these losses. Organic triazole compounds can be subject to losses due to biological degradation and must be replaced. Triazoles can be depleted as corrosion inhibitors by reaction with metal ions such as copper in solution.

In aqueous water systems, the concentration of triazole compounds is most commonly determined in the field using a colorimetric method involving the collection of a water sample, adding a series of reagents, and digesting the sample for several minutes using a strong UV light source, which produces a faint yellow color that can be correlated to the triazole concentration using a spectrophotometer or a handheld color comparator. Colorimetric methods are applied to discrete batch samples rather than being continuous. Moreover these types of methods would be difficult and expensive to automate, requiring sampling pumps, consumable reagents and pumps, and time delays during digestion stage. These factors make colorimetric assays of triazoles difficult to implement for in-line control.

In a well-equipped laboratory, the concentration of triazole compounds can also be determined by skilled chemists using high performance liquid chromatography (HPLC). HPLC involves injecting a known sample volume into a pumped eluent solution, which passes through a chromatography column and through a detector, generating a series of peaks on a chromatogram, which are evaluated and quantitated by the chemist. HPLC, however, may not be practical for in-line monitoring and control in industrial water systems.

UV fluorescence is another method for measuring and controlling the amount of organic azole corrosion inhibits. UV fluorescence offers the potential advantage of being reagent-free as the triazole compounds fluoresce to some extent when excited at the appropriate wavelength. UV fluorescence also offers the potential for rapid detection, which is more suitable for in-line process control.

However, the fluorescence signal of many triazole compounds, such as benzotriazole and tolyltriazole, are comparatively weak, making it difficult to detect their fluorescence from background fluorescence. A common method for overcoming this problem is to acidify the sample. The fluorescence of benzotriazole and tolyltriazole may be respectively increased by 6.4 and 10.6 times by acidifying the sample to a pH of 0.5.

Because most aqueous systems operate at neutral to slightly alkaline pH, acidification requires removal of a sample from the system and the addition of an acidic reagent to the sample to achieve the required sensitivity. In other words, the necessary acidic reagent typically cannot be added to the system. As a result, the requirement for an acidic reagent reduces the viability of this method for use in detecting, monitoring, and controlling amounts of the azole inhibitor throughout the system.

In addition to pH sensitivity, the fluorescent signal of the azoles also changes significantly in the presence of chlorine. Chlorine is the most common disinfectant used in aqueous systems. A stable control signal in the presence of chlorine or halogens would be desirable to achieve precise control in many aqueous systems.

SUMMARY

In one aspect, this disclosure provides a method for inhibiting corrosion of a corrodible metal surface that contacts water in a water system. The method may include adding to the water a treatment composition including an ex-situ halogenated triazole compound. The halogenated triazole compound may be provided in an amount and for a time sufficient for inhibiting corrosion of a metal surface in contact with the water.

In another aspect, this disclosure provides a method of measuring a concentration of an ex-situ halogenated triazole compound provided in water in a water system for inhibiting corrosion of a corrodible metal surface that contacts the water in the water system. The method may include inducing the halogenated triazole compound to fluoresce, for example, by applying an amount of energy to the water such that the halogenated triazole compound fluoresces. Then, the intensity of the fluorescence emitted from the water may be measured to determine the concentration of the halogenated triazole compound in the water. This may be done, for example, by using a predetermined standard curve that compares the fluorescence intensity at a certain wavelength to the concentration of the halogenated triazole compound.

In another aspect, this disclosure provides a method of monitoring and controlling a concentration of an ex-situ halogenated triazole compound in water in a water system. The method may include inducing the halogenated triazole compound to fluoresce, and measuring an intensity of fluorescence emitted from the water according to the techniques described above. Then, based on the measured intensity, the concentration of the halogenated triazole compound may be adjusted.

DETAILED DESCRIPTION OF EMBODIMENTS

Figure 1:
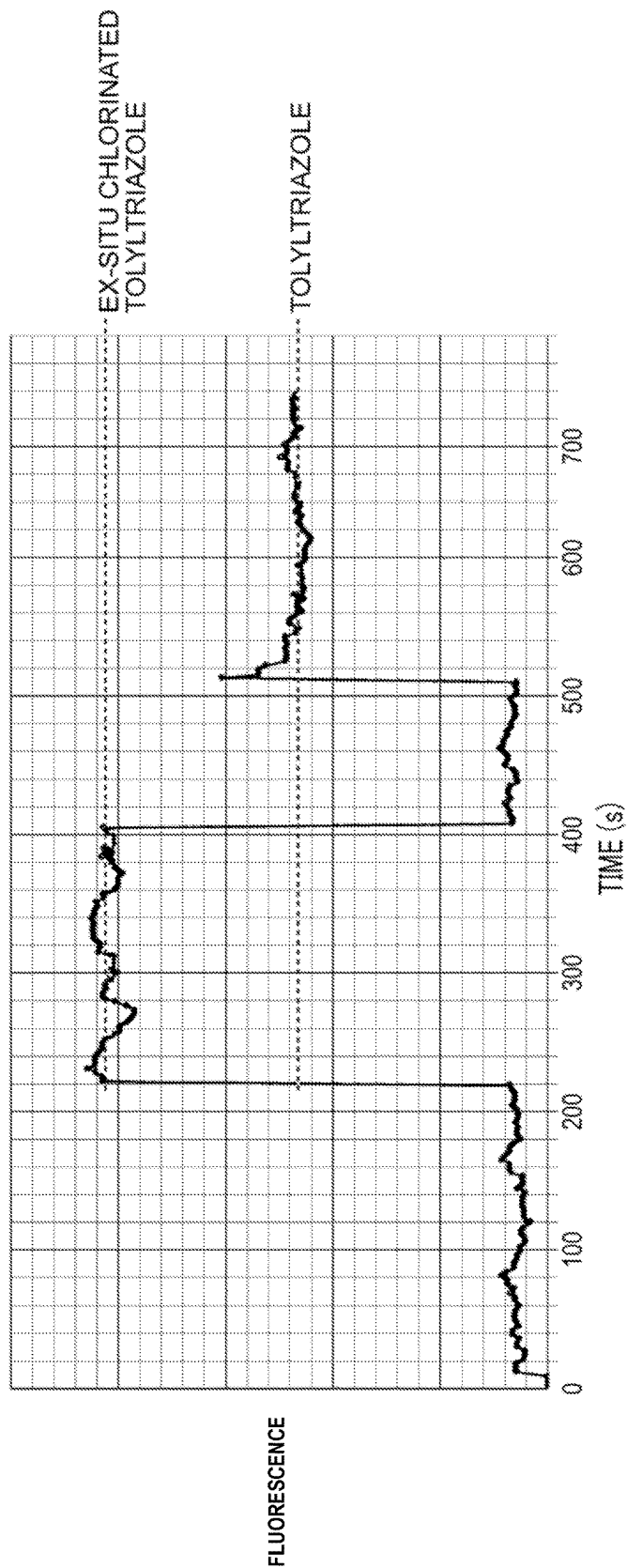
FIG. 1 is a graph showing the fluorescence intensities over time of 1 ppm tolyltriazole and 1 ppm ex-situ chlorinated tolyltriazole.

Embodiments of the disclosed methods relate to inhibiting corrosion of metal surfaces in a water system and measuring, monitoring, and controlling amounts of a corrosion inhibitor in water in the water system.

Embodiments disclosed herein include a method of inhibiting corrosion of a corrodible metal surface that contacts water in a water system. The method may include introducing into the water a treatment composition including an ex-situ halogenated triazole compound. The halogenated triazole compound may be provided in an amount sufficient for inhibiting corrosion of the metal surface, for example, in an amount sufficient to form a protective film on the metal surface. For example, the halogenated triazole may be provided in an amount of about 0.1 to about 500 ppm, about 0.1 to about 100 ppm, about 0.2 to about 50 ppm, about 0.5 to about 20 ppm, about 0.5 to about 10 ppm, or about 1 to about 5 ppm.

The triazoles may include, for example, benzotriazole, tolyltriazole, naphthotriazole, mercaptobenzothiazole, butylbenzotriazole, and salts thereof. Other triazoles may be used to the extent they exhibit corrosion inhibition of metal surfaces. The respective structures of benzotriazole and tolyltriazole (mixture of 4- and 5-isomers) are shown below.

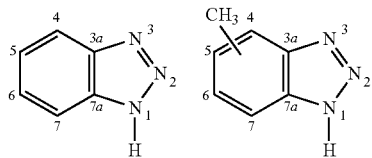

The halogen may include, for example, chlorine, fluorine, bromine, iodine, and aqueous salts thereof. The halogen may also include haloalkyls, such as trifluoromethyl. The triazoles, such as benzotriazole and tolyltriazole, may be halogenated at carbon number 6 and/or 7 in one embodiment. The halogenated triazoles may be prepared ex-situ by reacting a triazole with a halogenating agent before being introduced to the system component or stream that requires corrosion inhibition. The halogenating agent may be, for example, sodium hypochlorite. A high concentration sodium hypochlorite solution may be added to a slurry of the triazole, as discussed in more detail below. For example, from about 0.5 to about 40 wt. %, from about 0.5 to about 25 wt. %, from about 1 to about 15 wt. %, from about 3 to about 13 wt. %, or from about 3 to about 12 wt. % sodium hypochlorite solution may be used. Other halogenating agents may include, for example, $Cl_2$ (chlorine "gas"), chlorinated cyanuric acid, halogenated hydantoin, N-chlorosuccinimide, trityl chloride, 2-chloro triphenyl methyl chloride, $Br_2$, BrCl, hypobromite, sodium bromide, bromo chloro hydantoin, sodium bromide, bromo succinimide, bromo phthalimide, 1,3-dibromo-5,5-dimethyl hydantoin, hydrogen fluoride, xenon difluoride, cobalt(III) fluoride, and other chlorine, bromine, fluorine, and iodine donors. When the source of bromine is $Br_2$, BrCl, bromochloro hydantoin, or sodium bromide, the halogenating agent may be used in conjunction with an oxidant capable of producing chlorine.

The triazoles may be efficiently halogenated by first heating a slurry of the triazole, such as benzotriazole or tolyltriazole, to a temperature in a range from about 25 to about 80° C., from about 25 to about 55° C., from about 30 to about 50° C., or from about 35 to about 45° C. After heating, a stoichiometric amount of the halogenating agent, such as sodium hypochlorite solution, may be slowly added to the slurry while mixing. The pH of the slurry may be elevated to a pH in a range from about 9 to about 12, from about 10 to about 12, or from about 11 to about 12. The pH may be elevated, for example, by using sodium hydroxide.

Once the halogenated triazole is prepared ex-situ, the halogenated triazole may be added to the water in a water system in an amount that is sufficient for inhibiting corrosion of a metal surface in contact with the water, or may otherwise be introduced to the system component or stream requiring corrosion inhibition. Common industrial metals used in water systems include steel, copper, and zinc galvanized surfaces, which are corrodible. The halogenated triazole may be added to the water in an amount sufficient for forming a protective film on the metal surface to prevent and reduce corrosion damage.

Some disadvantages of non-halogenated triazole compounds as corrosion inhibitors include, for example, their comparatively weak fluorescence signals, which are further reduced in the presence of chlorine (a common disinfectant used in water systems), can be overcome by ex-situ halogenation of the triazoles before introducing them into water in a water system. The resulting halogenated triazole can exhibit a stronger fluorescence signal upon excitation than triazoles that have not been halogenated, and can also be more stable in water systems of interest. FIG. 1 shows that ex-situ chlorinated tolyltriazole emits a much stronger fluorescence signal that does the same amount of tolyltriazole.

As a result of the stronger fluorescence of halogenated triazoles, the fluorescence emitted by excited halogenated triazoles can be more readily detected from the background fluorescence without requiring the addition of an acidic reagent. Thus, in one aspect, the fluorescence of the ex-situ halogenated triazole compounds can be measured and continuously monitored in the water in the water system without requiring that a sample be taken from the water and without requiring the addition of an acidic reagent. As discussed in more detailed below, because the concentration of the ex-situ halogenated triazole compound can be determined from the fluorescence intensity of the halogenated triazole, the concentration of the halogenated triazole in the water in a water system can also be continuously monitored and controlled.

Figure 2A:
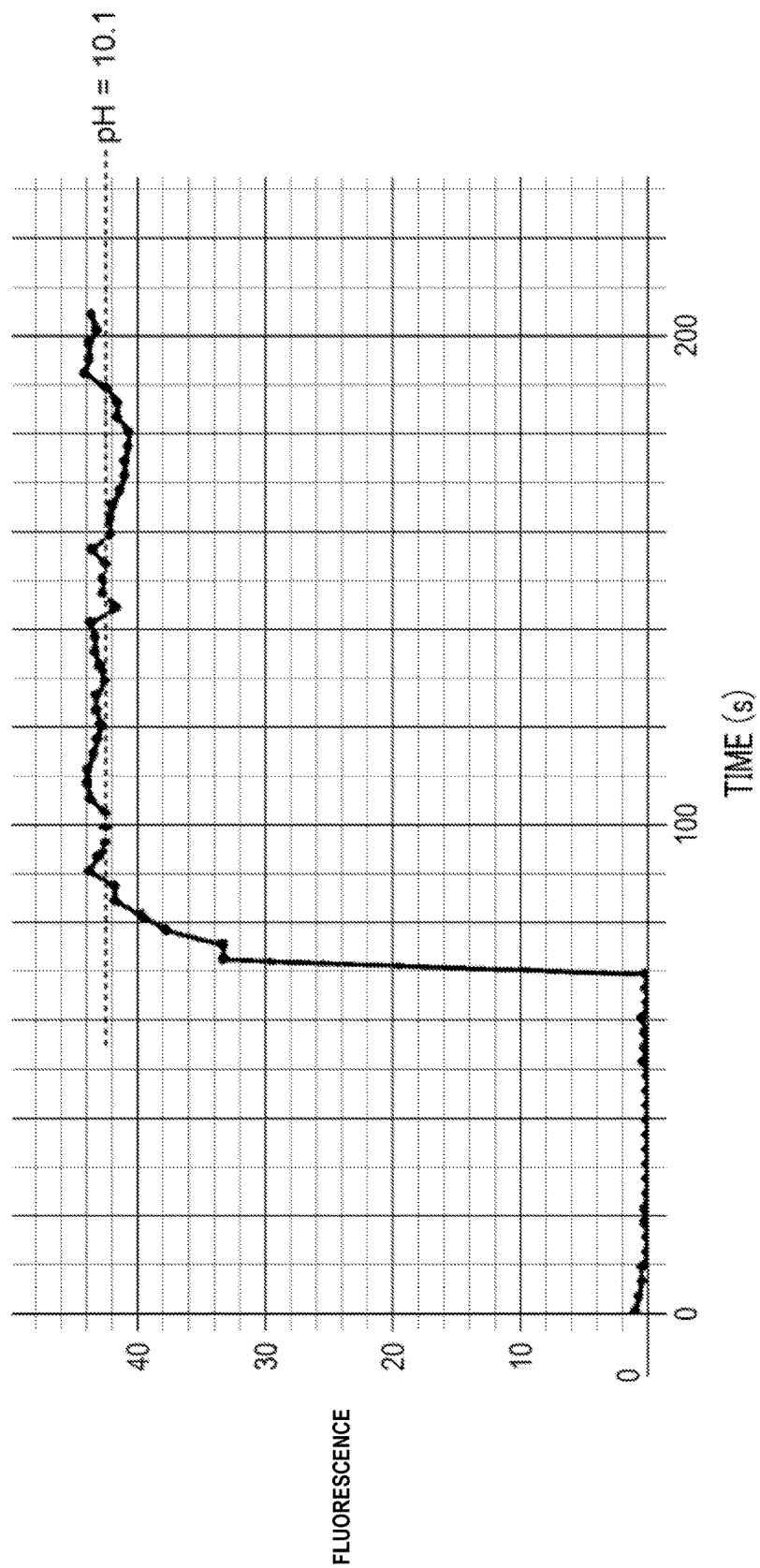
FIGS. 2A-C are graphs showing the fluorescence intensities over time of ex-situ chlorinated tolyltriazole at varying pH levels.
Figure 2B:
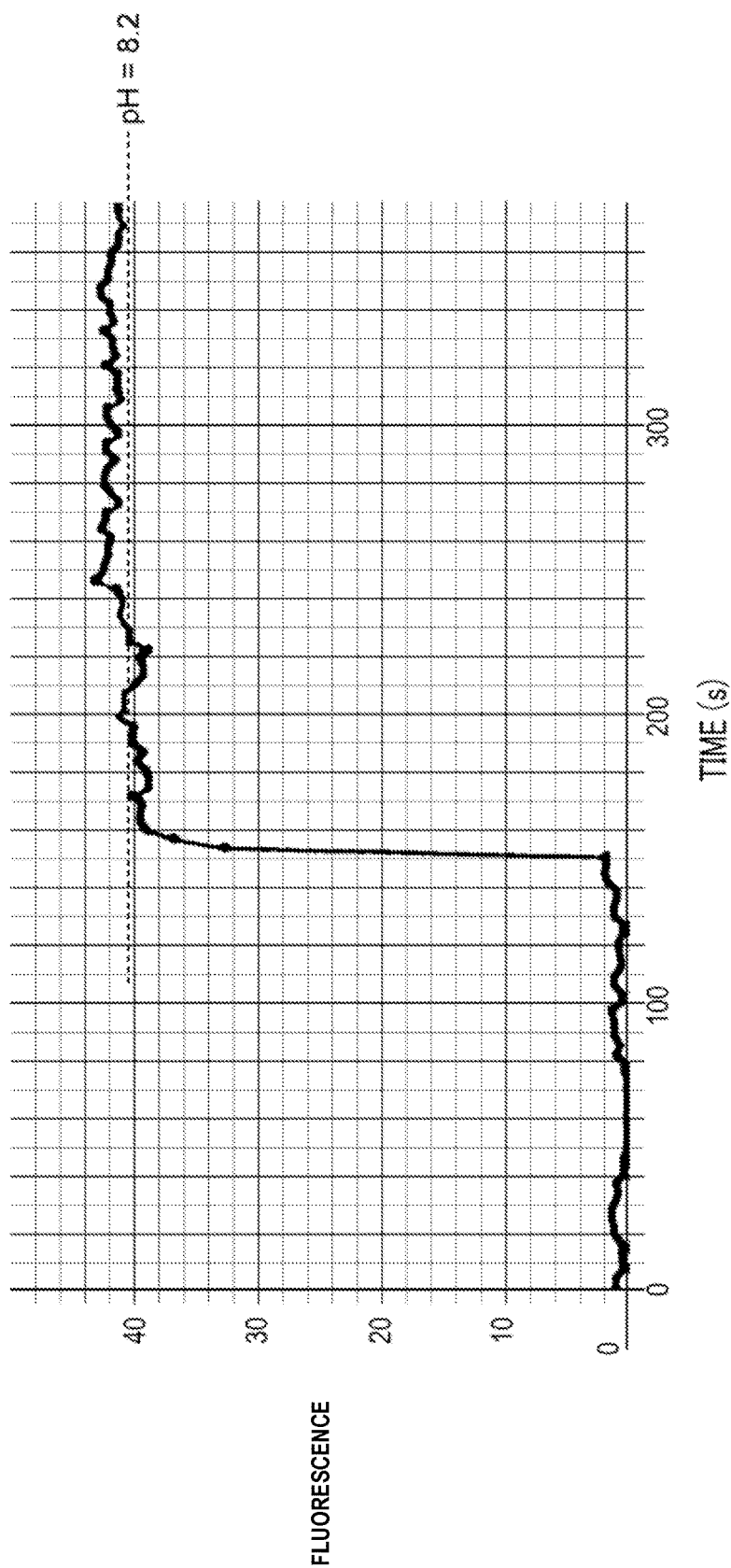
Figure 2C:
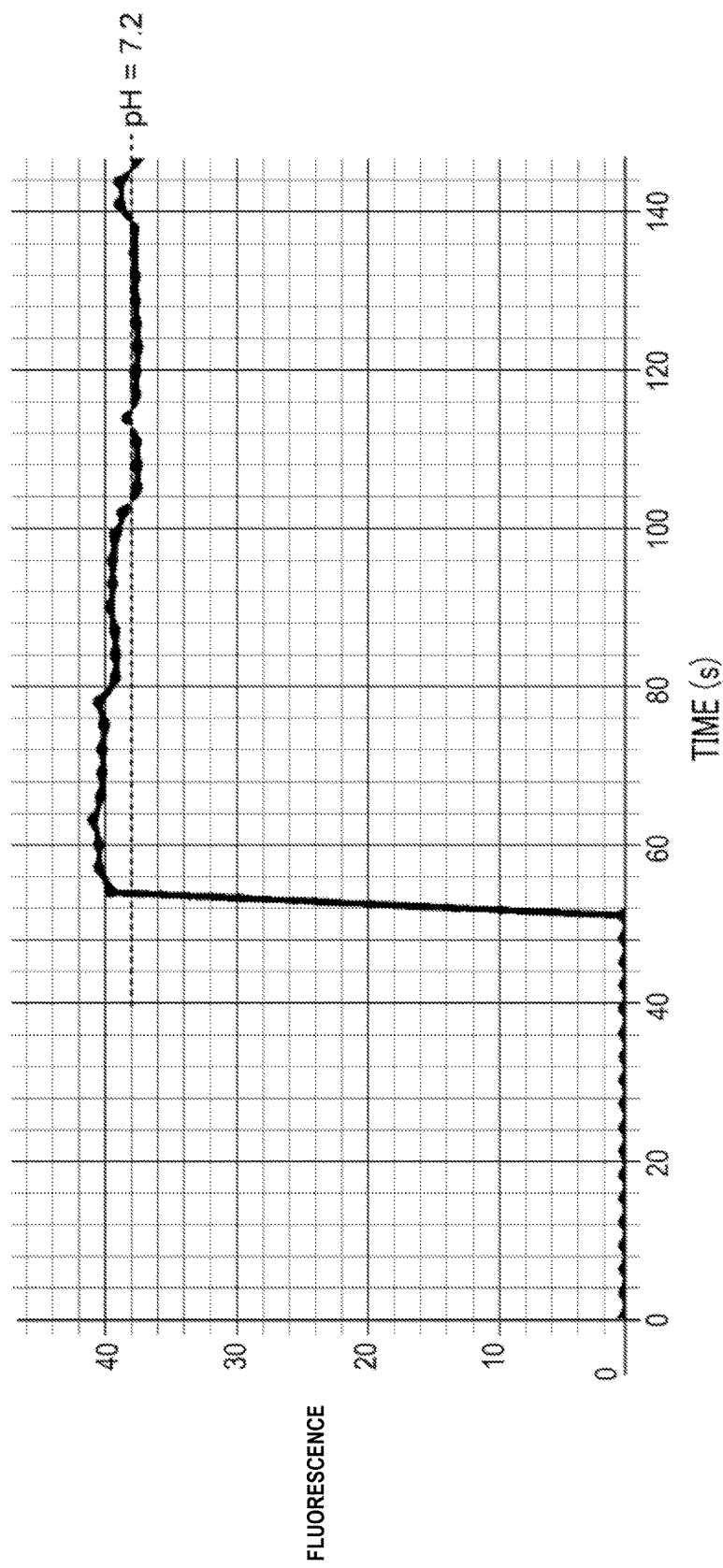

Additionally, the fluorescent signal of halogenated triazoles is maintained across a broad range of pH levels. In particular, the fluorescent signal of halogenated triazoles is maintained at varying pH levels in the range of interest for water systems, for example, from about 5 to about 12, from about 6 to about 11, or from about 7 to about 10. FIGS. 2A-C demonstrate that the fluorescent signal of halogenated triazoles measured with a 280/365 (Excitation/Emission) fluorometer is essentially independent of pH and remains substantially constant across a pH range of about 7 to about 10 (i.e., deviating by less than 10%). This eliminates the need for buffering or adjusting the pH of the aqueous solution. The aqueous system may be an industrial water system used for cooling or heating, for example.

Figure 3:
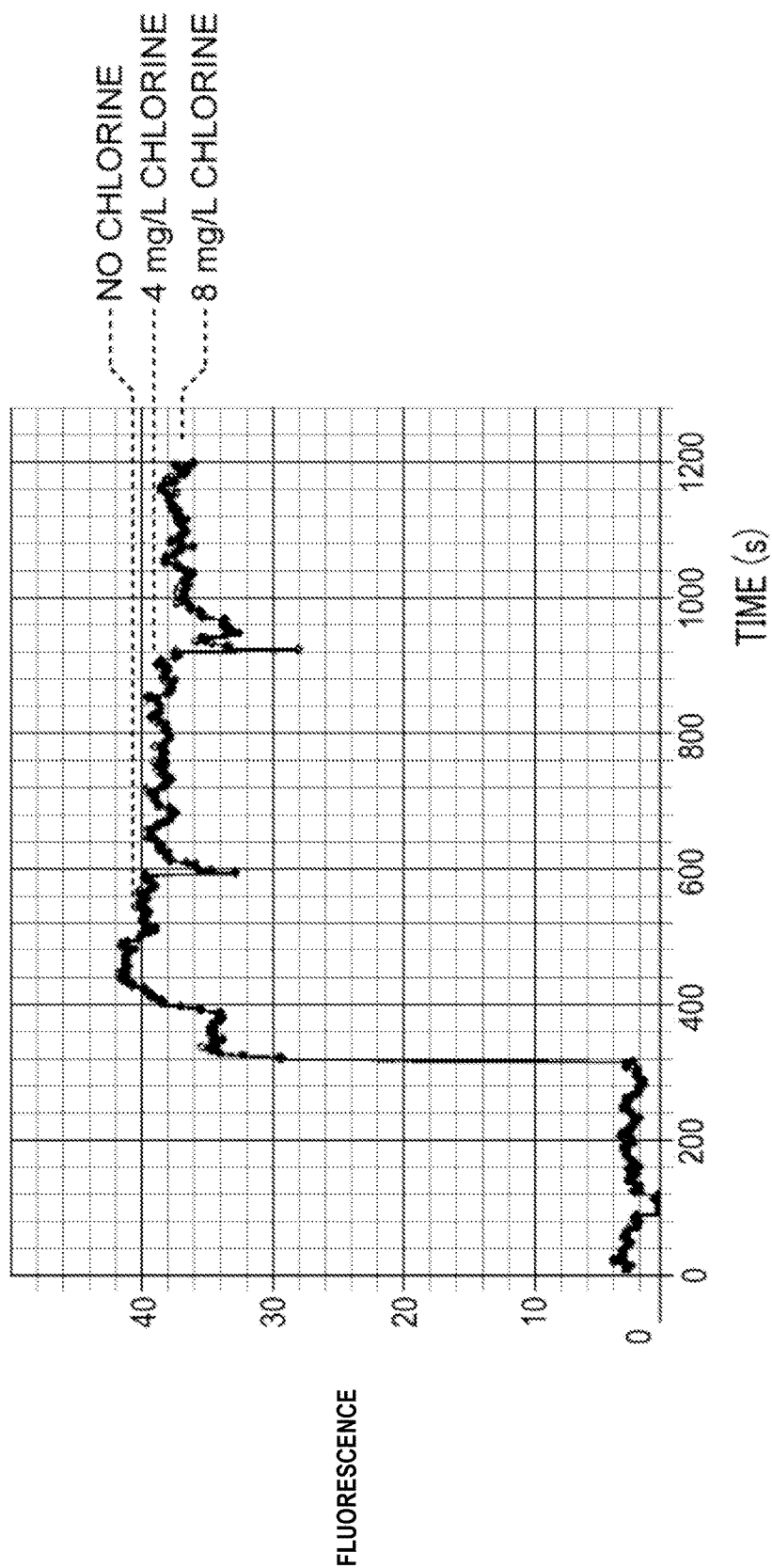
FIG. 3 is a graph showing the fluorescence intensity over time of ex-situ chlorinated tolyltriazole in the presence of varying concentrations of chlorine.
Figure 4:
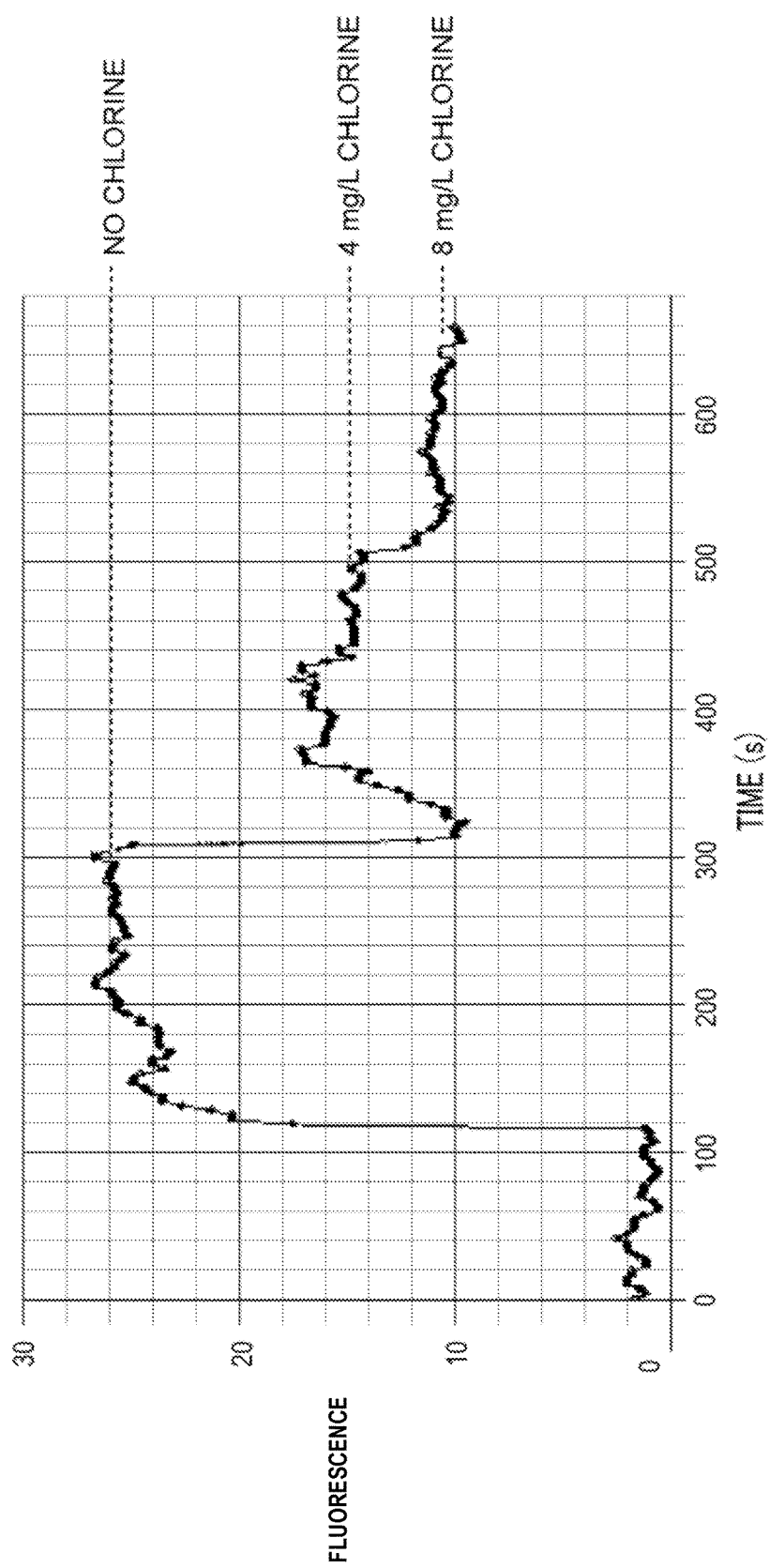
FIG. 4 is a graph showing the fluorescence intensity over time of tolyltriazole in the presence of varying concentrations of chlorine.

Unlike triazoles that have not been halogenated, ex-situ halogenated triazoles exhibit little to no change in fluorescent signal upon exposure to chlorine. For example, the chlorine may be present in the water in an amount in a range from about 0.1 to about 100 mg/L, from about 0.1 to about 25 mg/L, from about 1 to about 18 mg/L, or from about 3 to about 12 mg/L. FIG. 3 demonstrates negligible to no change in the fluorescent signal of ex-situ chlorinated tolyltriazole in response to 4 mg/L and 8 mg/L of chlorine. In contrast, FIG. 4 shows a 60% decrease in the fluorescent signal of non-halogenated tolyltriazole in the presence of 8 mg/L of chlorine as well as a significant decrease in the fluorescent signal of non-halogenated tolyltriazole in the presence of 4 mg/L of chlorine.

It was surprisingly discovered that the halogenated triazoles are very effective corrosion inhibitors, and remain as effective or more effective than their non-halogenated counterparts, even in the presence of chlorine. Also, as explained in greater detail below, the concentration of halogenated triazoles in the water can be conveniently measured and continuously monitored and controlled to be within a desired predetermined range.

Embodiments of the disclosed methods also relate to a method of measuring an amount of an ex-situ halogenated triazole compound in water in a water system. The method may include inducing the halogenated triazole compound to fluoresce. This may be done by applying an amount of energy to the water in the water system. The energy may be in the form of electromagnetic radiation, such as ultraviolet (UV) light, at a particular wavelength suitable for exciting the halogenated triazole compound. Electromagnetic radiation may also include infrared or visible light. Upon excitation, the halogenated triazole compound emits a detectable fluorescent signal.

For example, the absorption of light by the halogenated triazole compound at a certain wavelength can be measured as the compound's excitation signal, or the emission of light at a certain wavelength after the compound has been exposed to an excitation wavelength can be measured as the compound's emission signal. The fluorescent signal can be measured at a wavelength that corresponds to the peak intensity of emission or excitation. The halogenated triazole compound can have an excitation wavelength in a range of about 260 to about 300 nm, about 270 to about 290 nm, or about 275 to about 285 nm. For example, the halogenated triazole compound can exhibit peak excitation at a wavelength of 280 nm. The halogenated triazole compound may have an emission wavelength in a range of about 340 to about 390 nm, about 350 to about 380 nm, or about 360 to about 370 nm. For example, the halogenated triazole compound may exhibit peak emission at a wavelength of 365 nm.

A standard curve can be determined from the relationship between the intensity of the fluorescent signal and the concentration of the halogenated triazole compound so that the amount of the halogenated triazole compound in the water system can be quantified. For example, to determine the standard curve, the fluorescent signal of water in the presence of various known concentrations of the halogenated triazole compound are measured at the wavelengths at which the halogenated triazole compound exhibits peak excitation and/or emission. The intensity of the signals is plotted against the concentration of the halogenated triazole compound, and a regression of these data points is performed.

The embodiments of the disclosed methods allow for the real-time detection and quantification of the halogenated triazole compound in the water. Detection and quantification of the halogenated triazole can therefore be achieved more quickly, at a lower cost, and without the need for sophisticated equipment and training. This allows for greater control of the quantity of corrosion inhibitor that is added to the water system, both to ensure that sufficient corrosion inhibitor is present to prevent undesirable corrosion and to ensure that too much corrosion inhibitor is not added to the system, for example, for cost reasons and to prevent excess corrosion inhibitor from being present in waste streams.

Embodiments of the disclosed methods also include a method of measuring, monitoring, and controlling a concentration of the ex-situ halogenated triazole compound in water in the water system. The method may include inducing the halogenated triazole compound to fluoresce and measuring an intensity of the fluorescence emitted from the water to determine the concentration of the halogenated triazole compound by any of the techniques discussed above. Then, the concentration of the halogenated triazole compound may be compared to a minimum or maximum threshold level or to a predetermined concentration range that is sufficient for inhibiting corrosion of a corrodible metal surface that contacts the water in the water system. The method may also include adjusting the concentration of the halogenated triazole compound to be within a predetermined range for effectively inhibiting corrosion if the concentration is not within that range.

The concentration of the halogenated triazole compound in the water may be adjusted, for example, by increasing or decreasing the concentration of the halogenated triazole compound in the water. For example, the concentration of the halogenated triazole compound may be increased by adding additional halogenated triazole compound into the water. The concentration of the halogenated triazole compound may be decreased, for example, by adding more water into the water system and/or by discontinuing at least temporarily the addition of the halogenated triazole compound into the water to allow the concentration of the halogenated triazole compound to decrease due to consumption or loss of the halogenated triazole compound. For example, consumption or loss of the halogenated triazole compound may occur due to adsorption onto metal surfaces, reaction with soluble metals, and biological degradation. The addition of water into the water system to decrease the concentration of the halogenated triazole compound may continue until the concentration of the halogenated triazole compound is within the predetermined range. The addition of the halogenated triazole compound into the water may be discontinued until the concentration thereof is below the predetermined range. At that time, additional halogenated triazole compound may be added to the water to increase the concentration thereof to be within the predetermined range.

The above process may be repeated until the concentration of the halogenated triazole compound is determined to be within the predetermined concentration range. The predetermined concentration range may be any range within a range of about 0.1 ppm to 100 ppm, 0.1 to about 20 ppm, about 0.5 to about 10 ppm, or about 1 to about 5 ppm. The fluorescence intensity of the water may be continuously checked to continuously determine and monitor the concentration of the halogenated triazole compound and make the appropriate adjustments to the concentration as needed to ensure effective corrosion inhibition.

Other components in the water system or in the treatment composition may interfere with the fluorescent signal. For example, a component that interferes with the fluorescent signal of the halogenated triazole compound may be unsuitable for use in the water system or the treatment composition. To ensure a component's utility for a particular water system, the component's fluorescent signal can be measured in the presence of the halogenated triazole compound and other substances present in the water system.

For example, many substances in industrial water systems may fluoresce when excited by, for example, a 280 nm UV light, resulting in the potential for interference with excitation signal of the halogenated triazole compound. The isosbestic emission window of 365 nm+/−10 nm may be suitable for measuring the fluorescence of ex-situ halogenated triazoles. The 365 nm region is largely free of interference from other fluorescent substances, including other fluorescent compounds that may be intentionally added to the aqueous system.

Figure 5:
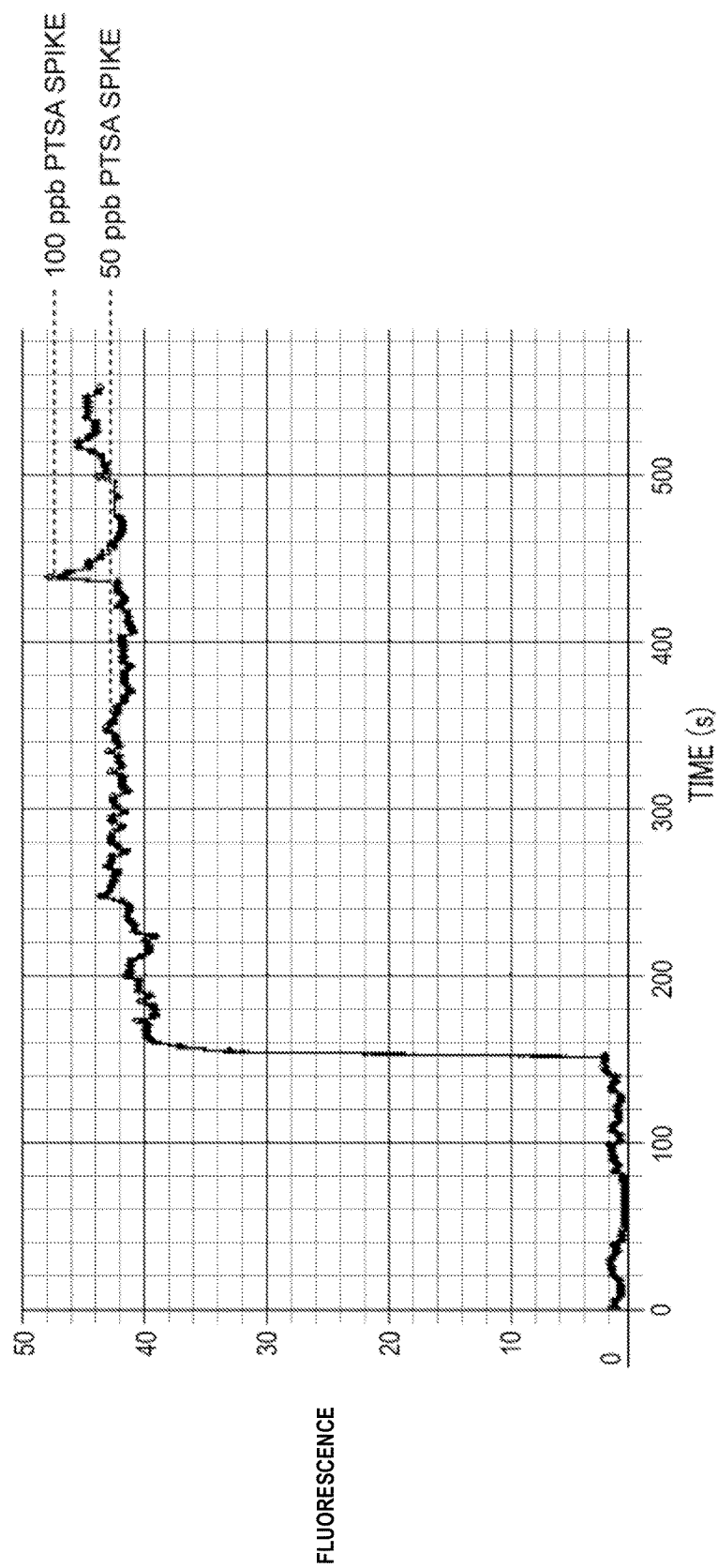
FIG. 5 is a graph showing the fluorescence intensity over time of ex-situ chlorinated tolyltriazole in the presence of 1,3,6,8-pyrenetetrasulfonic acid (PTSA).

In some embodiments, additional fluorescent compounds may also be employed in the treatment composition for tracking and controlling the addition rate of the halogenated triazole into the aqueous system. For example, 1,3,6,8-pyrenetetrasulfonic acid (PTSA), naphthalenedisulfonic acid, fluorescein, rhodamine, including rhodamine B and rhodamine 6G, and salts thereof are commonly used fluorescent tracing compounds in aqueous systems. Optical brighteners, for example, 4,4'-diamino-2,2'-stilbenedisulfonic acid, umbelliferone, 4,4'-bis(benzoxazolyl)-cis-stilbene, 2,5-bis(benzoxazol-2-yl)thiophene, and other stilbenes may also be used as a fluorescent tracer. In aqueous systems employing both the ex-situ halogenated triazole and another fluorescent compound, such as PTSA, the fluorescent signals of the two compounds should not interfere with one another. As shown in FIG. 5, there is no interference between the fluorescent signals of ex-situ chlorinated tolyltriazole and PTSA.

Thus, in one aspect, a substantially inert tracer, such as PTSA, may be used together with the ex-situ halogenated triazole in an aqueous system to allow the intensity of the two fluorescent signals to be compared. The rate of disappearance of the ex-situ halogenated triazole corrosion inhibitor relative to an inert tracer, such as PTSA, may provide valuable real-time information to the practitioner, for example, with respect to the consumption or loss of the corrosion inhibitor due to adsorption onto metal surfaces, reaction with soluble metals, and biological degradation. By using an inert fluorescent racer in combination with the ex-situ halogenated triazole compound, the relative rate of disappearance or consumption of the ex-situ halogenated triazole may be determined.

Figure 6:
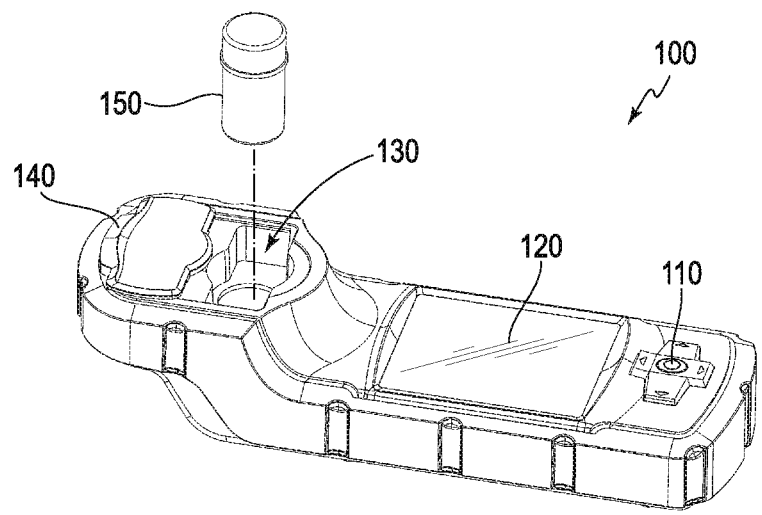
FIG. 6 is a perspective view of a handheld fluorometer for detecting fluorescence from a sample.

Embodiments of the method may also involve the addition of an ex-situ halogenated triazole corrosion inhibitor to an aqueous system and detecting it with a non-reagent fluorescence-based detection device. As described above, the ex-situ halogenated triazole is uniquely suited for non-reagent based detection by fluorescence. The fluorescence detector may be a portable handheld device that measures amounts of the corrosion inhibitor in discrete samples without the use of reagents. An example of such a fluorescence detector 100 is illustrated in FIG. 6. Such a portable handheld device is not currently commercially available for the excitation wavelength of 280 nm. A prototype is illustrated in FIG. 6. The fluorometer for detecting the ex-situ halogenated triazole compound may have an excitation wavelength in a range of about 260 to about 300 nm, about 270 to about 290 nm, or about 275 to about 285 nm. The fluorometer may also detect an emission wavelength in a range of about 340 to about 390 nm, about 350 to about 380 nm, or about 360 to about 370 nm. Knowing the concentration of the corrosion inhibitor permits an operator to adjust the dosage rate of the inhibitor to maintain the concentration within the desired predetermined range in the aqueous system.

The exemplary fluorescence detector 100 illustrated in FIG. 6 includes, for example, a navigational control pad 110, a display 120, a sample vial compartment 130, a sample vial 150, and a light shield cover 140. The navigational control pad 110 may include any input interface that allows a user to input commands and/or interact with the fluorometer 100. For example, the control pad 110 may be in the form of a keypad. The control pad 110 may, for example, allow an operator to enter variables, set parameters, access menu items, and the like. The display 120 may be, for example, a liquid crystal display (LCD), or any other suitable display. The display 120 may display sensor readings, calculations, and any other information to the user. The sample vial compartment 130 houses the sample vial 150, which contains the sample to be tested. The fluorescence detector may include any additional suitable components and configurations.

Figure 7A:
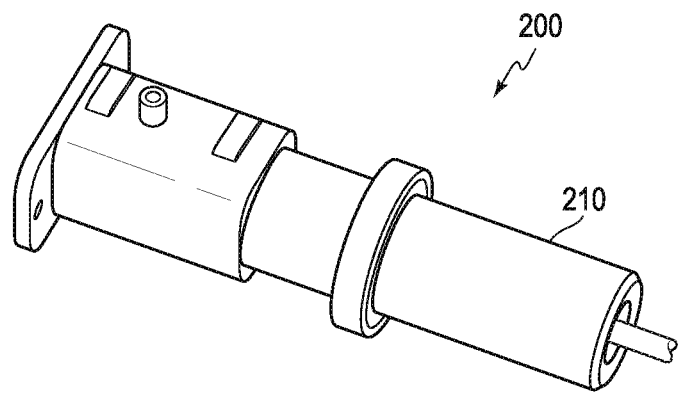
FIGS. 7A and 7B are perspective views of a fluorometer in a probe-in-tee-configuration for mounting in a water system.
Figure 7B:
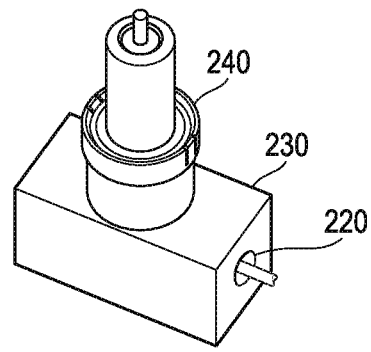
Figure 7C:
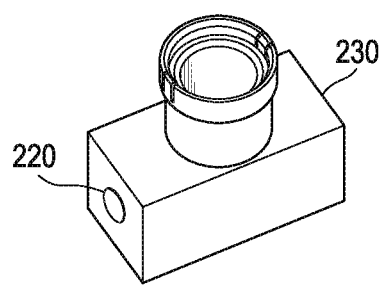
FIG. 7C is a perspective view of a mounting tee for receiving and mounting a fluorometer probe in a water system.
Figure 8:
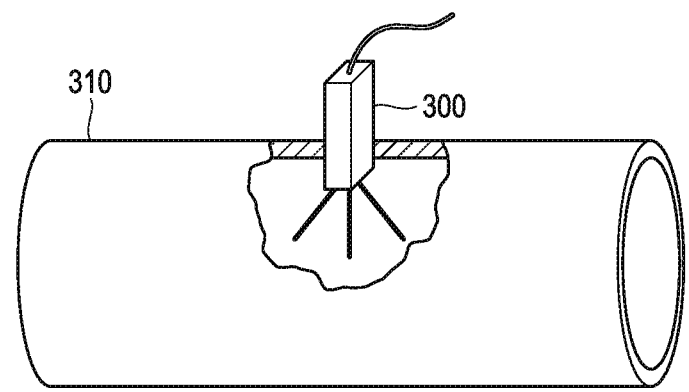
FIG. 8 is a schematic diagram illustrating an in-line fluorometer directly mounted in a stream for monitoring the fluorescence of that stream.
Figure 9:
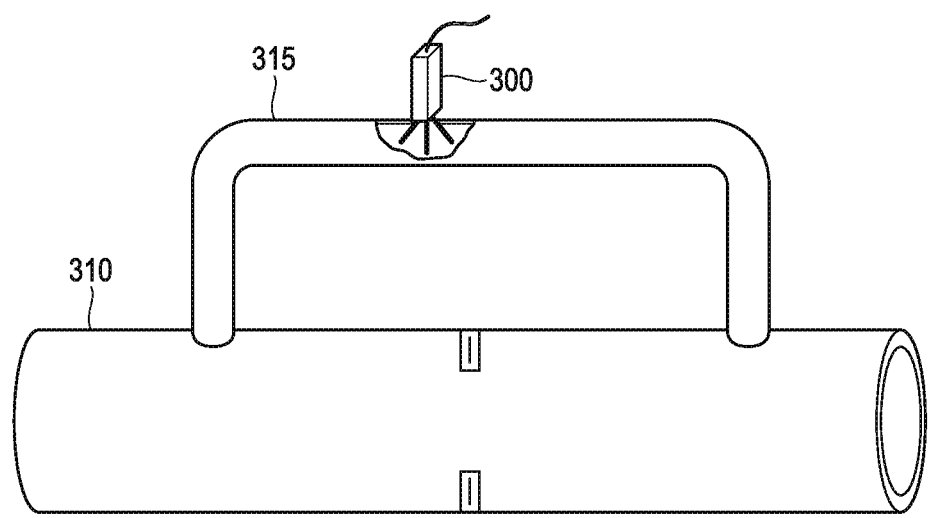
FIG. 9 is a schematic diagram illustrating an in-line fluorometer mounted in a slipstream of a flowing stream for monitoring the fluorescence of the flowing stream.

Embodiments may also use a detector that is an in-line unit, for example, as shown in FIG. 7. The in-line detector may be mounted either directly in the water stream, as shown in FIG. 8, or may be mounted on a slipstream, as shown in FIG. 9. The in-line detector, operating without the need to add other reagents, may directly measure the concentration of the corrosion inhibitor on an essentially continuous basis with respect to the mean residence time in the system. The in-line detector is not currently commercially available for the wavelengths required for the ex-situ halogenated triazole. The in-line detector may be coupled to electronic devices capable of receiving the signal from the detector, interpreting the signal and relating it to the concentration of the corrosion inhibitor.

For example, the in-line fluorescence detector 200 illustrated in FIG. 7 includes a probe-in-a-tee configuration in which the probe 210 is installed in a mounting tee 230. In the embodiment illustrated in FIG. 7, the mounting tee 230 includes seal 240 to seal the probe in the mounting tee 230. The seal 240 may be, for example, an O-ring compression seal to avoid leakage or any other suitable seal. The mounting tee 230 includes a threaded portion 220 for in-line installation in the water system. For example, the threaded portion 220 may be a male or female threaded portion. The mounting tee 230 including the probe 210 may be installed in-line via a threaded attachment between the threaded portion 220 of the tee 230 and a threaded portion of a pipe of the water system. The threaded portion 220 may be, for example ¾ inch NPT or any other suitable threaded portion. The probe 210 should be installed into the mounting tee 230 such that it protrudes into the stream in the pipeline to achieve an accurate measurement. Although the in-line fluorescence detector 200 is illustrated in FIG. 7 as a probe-in-a-tee configuration, the in-line fluorescence detector may be in any suitable configuration for in-line installation in a water system to measure fluorescence of the water stream.

As shown in FIG. 8, the in-line detector 300 may be mounted either directly in the pipeline 310 of the water system through which the water stream flows. In another embodiment, the in-line detector 300 may be mounted on a slipstream 315 of the water system, as shown in FIG. 9.

For example, the fluorometer may be an in-line device that emits a signal in relation to the measured concentration of ex-situ halogenated triazole. The process may include: introducing the ex-situ halogenated triazole into the aqueous system to treat a water stream; directing the treated water past a suitable fluorometer; correlating the intensity of the fluorescent signal to the concentration of the ex-situ halogenated triazole; optionally conducting such measurements on a frequency that is substantially continuous with respect to the characteristic time constant of the aqueous system; and conveying the measured values electronically to a device capable of interpreting the values and triggering an appropriate reaction from a device configured to dose the water with the ex-situ halogenated triazole. The fluorometer signal may be output to a device capable of displaying a readout proportional to the ex-situ halogenated triazole concentration. The fluorometer signal may be output to a device capable of controlling the dosage of the ex-situ halogenated triazole to the aqueous system. The signal may be output to a device capable of transmitting the signal to other external devices by wired or wireless transmission means.

The fluorescence signals may be processed by a device that includes a processor, such as those found in PC or laptop computers. The device can include a memory for storing standard curves, threshold value information, process information, etc. The processor can compare the measured fluorescence signals to a standard curve to determine the quantity of halogenated triazole in the system, can determine whether the measured quantity is within prescribed limits, and can send instructions for modifying process conditions based on the measured quantity, e.g., adding more or less of the halogenated triazole to the system. In this regard, the halogenated triazole compound can be kept in a container or tank and connected to the water system via a conduit with a valve that be controlled by instructions from the processor to increase or decrease the concentration of the halogenated triazole compound in the water.

The measured corrosion inhibitor concentration may be determined from the fluorescence intensity of the corrosion inhibitor, interpreted, and conveyed to a chemical dosing system, which automatically adjusts the dosing (e.g., by using signals to control a valve) to maintain the concentration of the corrosion inhibitor in the water within the predetermined desired concentration. The measured concentration of the corrosion inhibitor may also be conveyed to remote devices using standard wired or wireless communication protocols (FIG. 10).

Figure 10:
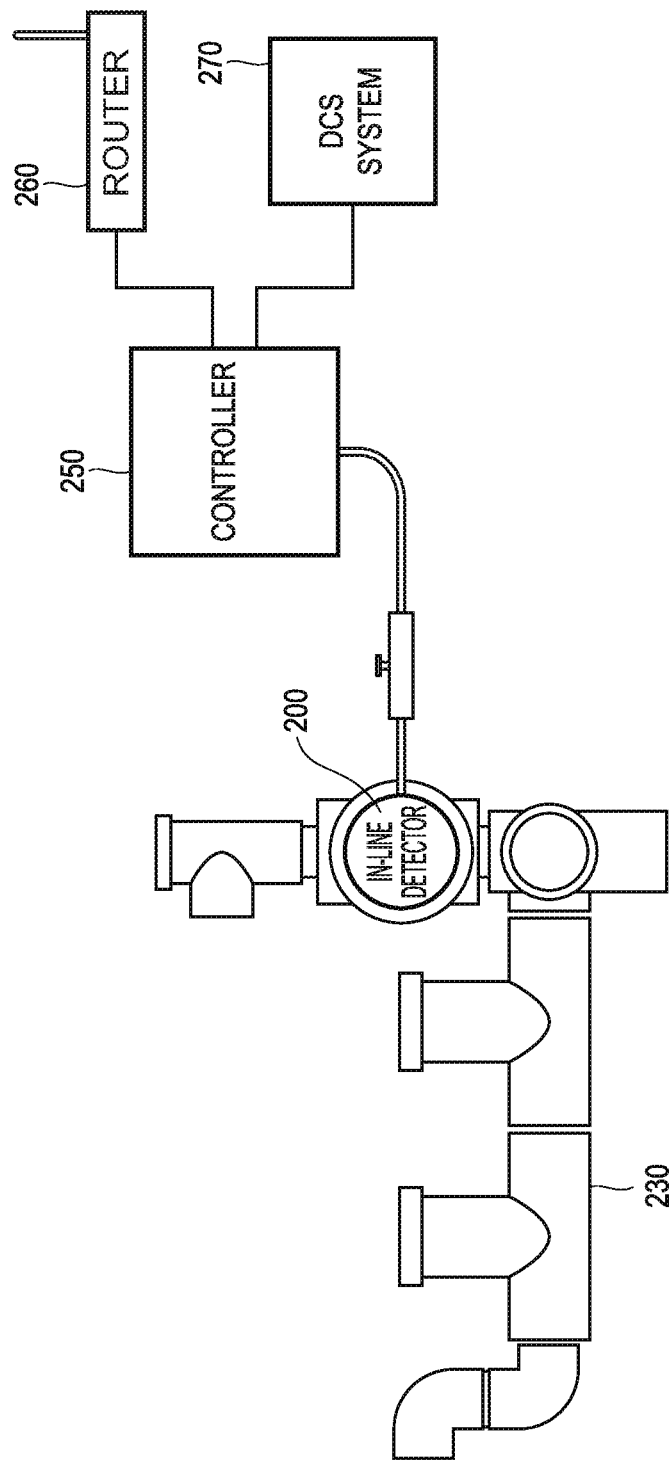
FIG. 10 is a diagram illustrating a fluorometer communication to a remote device.

As shown in FIG. 10, the in-line fluorescence detector 200 is installed in the water system via a mounting tee 230. The fluorescence detector 200 is connected to a controller 250, which is connected to a wireless router 260, and a distributed control system (DCS) system 270. The fluorescence measurements are sent to the controller 250 from the fluorescence detector 200. The controller 250 may include a display on which the fluorescence measurements and/or any other information may be displayed. The controller 250 may transmit the measurements and/or other information via either a wired or wireless connection to a processor and/or another controller within the DCS system 270. For example, the fluorescence measurements and/or other information can be transmitted from the controller 250 via the wireless router 260. A remote or local controller and/or processor within the DCS system 270 may receive the fluorescence measurements from the controller 250 and compare those measurements with a standard curve to determine the quantity of halogenated triazole in the system, and/or whether the measured quantity is within prescribed limits. If the amount of the halogenated triazole is not within the prescribed limits, the controller and/or processor within the DCS system 270 may send a command signal to the controller 250 or another controller increase or decrease the amount of the halogenated triazole being added to the water system. The controller 250 may display a warning to an operator that the amount of the halogenated triazole is not within the prescribed limits. An operator can manually adjust the amount of the halogenated triazole being added to the water system.

In another embodiment, the controller 250 may include a processor that compares the measured fluorescence signals to a standard curve to determine the quantity of halogenated triazole in the system, and/or whether the measured quantity is within prescribed limits. In this embodiment, the controller 250 may display and/or transmit to another controller and/or processor within the DCS system 270 the quantity of the halogenated triazole in the system, instead of the raw fluorescence measurements. If the amount of the halogenated triazole is not within the prescribed limits, the controller 250 may send a command signal to increase or decrease the amount of the halogenated triazole being added to the water system. The controller 250 may display a warning to an operator that the amount of the halogenated triazole is not within the prescribed limits. An operator may manually adjust the amount of the halogenated triazole being added to the water system.

The controller 250 may also include inputs to control the fluorescence detector 200 locally, or to locally control any other sensor or device that is connected to the controller 250. The controller 250 may also receive commands or other information from another controller or processor within the DCS system 270 to remotely control the fluorescence detector and/or any other sensor or device connected thereto. For example, other devices, such as an in-line corrosion rate measurement device 320 (shown in FIG. 12) may also be connected to the controller 250.

The fluorometer may be an in-line device that emits a signal in relation to the concentration of any additional fluorescent tracer(s) that may be present. Such a system is illustrated in, for example, FIG. 11. The process may include: dosing the aqueous system with additional fluorescent tracer(s) with a predetermined ratio with the ex-situ halogenated triazole compound to treat a water system; directing the treated water past a suitable fluorometer or fluorometers, such as fluorometers 300a and 300b in FIG. 11; determining the intensity of the fluorescent signal of the fluorescent tracer(s) to determine the concentration of the fluorescent tracer(s) and also to determine the intensity of the fluorescent signal associated with the ex-situ halogenated triazole to determine its concentration; correlating the concentration of the additional fluorescent tracer(s) to the concentration of ex-situ halogenated triazole to determine the relative loss or consumption of the ex-situ halogenated triazole; optionally conducting such measurements on a frequency that is substantially continuous with respect to the characteristic time constant of the aqueous system; and conveying the measured values electronically to a device capable of interpreting the values and displaying and conveying them to allow appropriate ex-situ halogenated triazole dosing decisions to be made.

Figure 11:
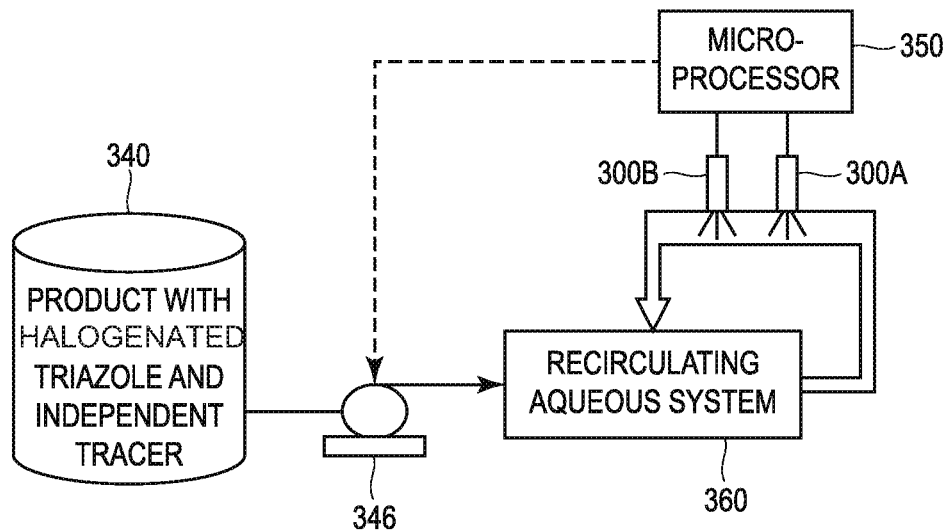
FIG. 11 is a schematic diagram illustrating a system using both an independent fluorophore and the ex-situ halogenated triazole.

The concentration of corrosion inhibitor may be correlated to the overall treatment composition dosage for the purpose of determining corrosion inhibitor degradation or reaction with surfaces and metal ions in the water. As discussed above, an independent fluorescent compound, which can be measured using a fluorescence detector without requirement for reagents, can also be added to the water system. Such devices are commercially available from companies, such as Pyxis-Labs, which apply tracing flows and product application rates to aqueous systems. By comparing the fluorescence signal from the independent tracer with the fluorescence signal from the ex-situ halogenated triazole, the loss of the corrosion inhibitor can be detected and quantified. Such an arrangement involving both an independent tracer and the ex-situ halogenated triazole is illustrated in FIG. 11. Two physically separate fluorescent sensors, such as a first fluorometer 300a and a second fluorometer 300b, may be used to detect the fluorescence of the independent tracer and the ex-situ halogenated triazole corrosion inhibitor, or the fluorescent sensors may be combined into a single housing using advanced optical detectors.

As shown in FIG. 11, the independent tracer and fluorinated triazole may be present in a container 340 that is connected to the recirculating water system 360. The fluorinated triazole and the independent tracer can be added into the recirculating aqueous system 360 via a valve 346. The valve 346 operates to control the dosing rate of the fluorinated triazole and the independent tracer in the water system. The valve 346 may open or close to control the dosing rate of the fluorinated triazole and independent tracer into the recirculating water system 360 based on signals from a processor 350. The processor 350 may be, for example, a microprocessor or any other suitable device. The processor 350 may send command signals to the valve to increase or decrease the amount of the fluorinated triazole and independent tracer added to the water system 360 depending on fluorescence measurements of the halogenated triazole and independent tracer received from the first and/or second fluorometer 300a and 300b.

The measurements from the fluorometer 300a and/or 300b may be transmitted to the processor or microprocessor 350. The processor 350 may contain an algorithm that compares the fluorescence signal from the independent tracer with the fluorescence signal from the ex-situ halogenated triazole to detect and quantify the loss of the corrosion inhibitor in the aqueous system 360. The processor 350 may control the dosing rate of the halogenated triazole compound and independent tracer to maintain the corrosion rate at the desired rate while optimizing corrosion inhibitor dosage. For example, the processor 350 may send a signal to the valve 346 to increase or decrease the amount of the halogenated triazole and independent tracer that is added to the water system 360 from the container 340 containing the halogenated triazole and independent tracer and connected to the water system 360 via the valve 346.

The fluorometers 300a and 300b may be individual units connected to a common logical processing device 350 capable of comparing the fluorescent signals from the additional fluorescent tracer(s) and the ex-situ halogenated triazole. The fluorometer 300 may be a single housing. The single housing may include: multiple excitation light-emitting diodes (LEDs) capable of supplying the appropriate excitation wavelengths for the ex-situ halogenated triazole and the additional fluorophore; a multiple band-pass filter capable of blocking emission wavelengths not associated with the ex-situ halogenated triazole or additional fluorophore; and/or an emissions wavelength detector sensitive to the emissions wavelength associated with the ex-situ halogenated triazole and the additional fluorophore.

In all embodiments, the fluorometer may compensate for background interference. Such an arrangement may include a separate fluorometer installed in the untreated source water to measure background interference, which is then read by a microprocessor and used to compensate for background fluorescence in the reading of the fluorometer measuring the ex-situ halogenated triazole. The compensation may be achieved by alternately passing untreated and treated waters through the same fluorometer using a valving mechanism. The fluorometer for measuring the fluorescence of the ex-situ halogenated triazole compound may also compensate for light scattering caused by turbidity in the treated water. The ex-situ halogenated triazole fluorometer and the additional fluorophore(s) fluorometer may compensate for interfering background fluorescence and turbidity. The fluorometer may also compensate for the fluorescence of one or more additional fluorescent tracers that are also added to the aqueous system.

In some embodiments, the same fluorometer can be used to measure both the untreated water background fluorescence and the ex-situ halogenated triazole fluorescence in the treated water. A valve switching mechanism can be used to select the untreated water or the treated water. The signals measured from the untreated water and treated water can be read by a microprocessor and a correction can be carried out according to a formula.

For example, naturally occurring substances, such as lignin and humic acid, may be present in natural water systems. Lignins and humic acids absorb 280 nm UV light, which may cause a negative inference in measuring the fluorescence of the ex-situ halogenated triazole. The fluorometer may be able to measure the amount of attenuation of the 280 nm excitation light and compensate the fluorescent signal loss. If the water causes a significant amount attenuation of the 280 nm excitation light, a spike and recovery experiment can be conducted and the degree of compensation could be adjusted based on the spike recovery result.

Although the naturally occurring substances fluoresce mainly at longer emission wavelength, they may variably contribute a small amount of fluorescence background in the 365 nm emission region. If the water is suspected of having a significant amount of naturally occurring substances with emissions in the 365 nm region, such as systems fed with untreated surface water, the background fluorescence of the untreated water at 280/365 (Ex/Em) may be measured to determine possible positive interference caused by these substances. A separate fluorometer can be installed to monitor the background fluorescence of the untreated water and compensate for it. The fluorometer used to monitor the interfering fluorescence can have the same excitation and emission wavelengths as that used to measure the fluorescence of the ex-situ halogenated triazole in the treated water.

To enhance the fluorescence signal of the ex-situ halogenated triazole compound by making it more distinguishable from the background fluorescence, the fluorometer can be constructed with a different excitation or emission wavelengths and be tuned intentionally to have higher sensitivity for the substances that cause interference with the ex-situ halogenated triazole measurement at 280/365 (Ex/Em).

In some embodiments, multiple fluorometers, spectrophotometers, and/or turbidimeters may be used to monitor the absorbance at different wavelengths, fluorescent signals at a combination of different excitation and emission wavelengths, and light scattering intensities at different wavelengths of the cooling water. For example, these devices may include a 365/410 (Ex/Em) fluorometer for a fluorescent tracer, such as PTSA, or a 280/410 (Ex/Em) fluorometer, which has more sensitivity to the naturally occurring interfering substances than the 280/365 (Ex/Em) fluorometer. The information measured from the multiple detection devices can be used to determine the ex-situ halogenated triazole concentration and the concentration of other intentionally added fluorescent compounds.

The in-line concentration of the ex-situ halogenated triazole may be correlated to the output of an in-line linear polarization resistance (LPR)-based corrosion rate instrument. Such an arrangement may include an in-line fluorometer for the ex-situ halogenated triazole compound and an in-line LPR-based corrosion rate meter. The signals may be routed from the in-line fluorometer and the in-line LPR-based corrosion rate meter to a single processing device. The process device may contain an algorithm that correlates the concentration of the ex-situ halogenated triazole compound to the corrosion rate for the current condition of the aqueous system. The processing device may control the dosing rate of the halogenated triazole compound or treatment composition to maintain the corrosion rate at the desired rate while optimizing corrosion inhibitor dosage.

Figure 12:
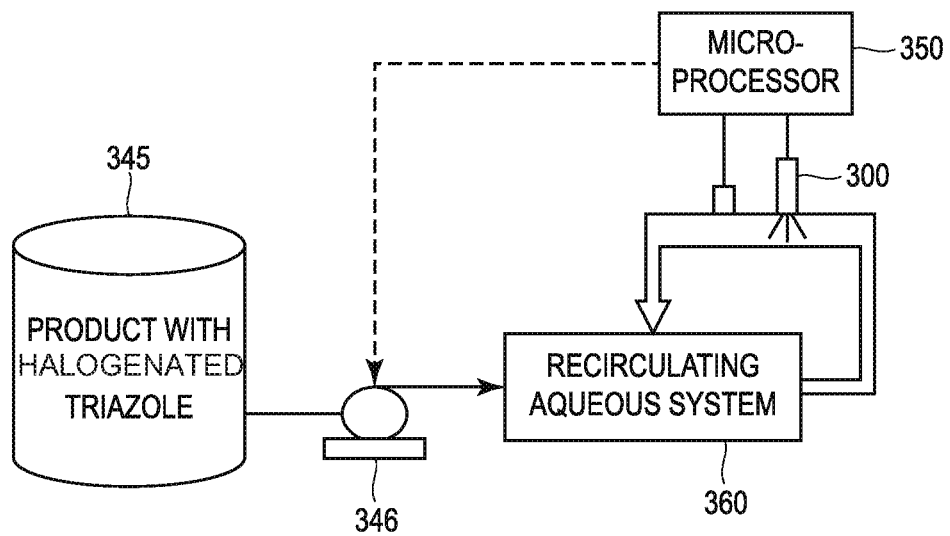
FIG. 12 is a schematic diagram illustrating a system with an in-line linear polarization resistance (LPR) corrosion rate measurement device.

As shown in FIG. 12, an in-line corrosion rate measurement device 320 may also be used. Such devices, based on the principle of linear polarization resistance (LPR), are commercially available from companies, such as Rohrback Cosasco and Pepperl Fuchs. By combining the fluorescent signal from the ex-situ halogenated triazole fluorometer 300 with an in-line corrosion rate measurement from the device 320, an adaptive algorithm relating the concentration of the corrosion inhibitor to the corrosion rate of the metal can be determined in real-time in response to changes in the corrosiveness of the aqueous system (FIG. 12).

As described above, the measurements from the fluorometer 300 and the corrosion rate measurement device 320 may be transmitted to a processor or microprocessor 350. The processor 350 may contain an algorithm that correlates the concentration of the ex-situ halogenated triazole compound to the corrosion rate for the current condition of the aqueous system. The processor 350 may control the dosing rate of the halogenated triazole compound or treatment composition to maintain the corrosion rate at the desired rate while optimizing corrosion inhibitor dosage. For example, the processor 350 may send a signal to the valve 346 to increase or decrease the amount of the halogenated triazole that is added to the water system 360 from a container 345 containing the halogenated triazole and connected to the water system 360 via the valve 346.

Although the fluorescence detectors 100, 200, and 300 (including 300a and 300b) have been described with respect to specific embodiments illustrated in FIGS. 6-9, any suitable device capable of detecting fluorescence and configurations thereof may be used.

It will be appreciated that the above-disclosed features and functions, or alternatives thereof, may be desirably combined into different systems or methods. Also, various alternatives, modifications, variations or improvements may be subsequently made by those skilled in the art. As such, various changes may be made without departing from the spirit and scope of this disclosure.

What is claimed is:

1. A method of measuring a concentration of an ex-situ halogenated triazole compound in water of a water system, the method comprising:
   inducing the halogenated triazole compound to fluoresce;
   measuring an intensity of fluorescence emitted from the water at a pH in a range of from 5 to 12; and
   determining the concentration of the halogenated triazole compound in the water based on the measured intensity,
   wherein the halogenated triazole comprises a triazole selected from the group consisting of benzotriazole, tolyltriazole, mercaptobenzothiazole, butylbenzotriazole, and salts thereof.

2. The method according to claim 1, further comprising adding to the water a treatment composition comprising the ex-situ halogenated triazole compound.

3. The method according to claim 1, wherein a pH adjusting agent is not added to the water to enhance the fluorescence of the halogenated triazole compound.

4. The method according to claim 1, wherein the concentration of the halogenated triazole compound in the water is determined by comparing the measured intensity of fluorescence to a standard curve defining the relationship between the intensity of fluorescence of the halogenated triazole compound and the concentration of the halogenated triazole compound.

5. The method according to claim 1, wherein the intensity of fluorescence is measured by an in-line fluorescence detector mounted in a main water stream or a slipstream of the water system.

6. The method according to claim 1, wherein the intensity of fluorescence is measured by a handheld fluorescence detector.

7. The method according to claim 1, further comprising:
   adding an independent fluorescent tracer into the water in a predetermined ratio with the halogenated triazole compound;
   measuring an intensity of fluorescence of the independent fluorescent tracer;
   determining the concentration of the independent fluorescent tracer in the water based on the measured intensity; and
   correlating the concentration of the fluorescent tracer to the concentration of the halogenated triazole compound to determine the relative consumption of the halogenated triazole compound in the water.

8. A method of monitoring and controlling a concentration of an ex-situ halogenated triazole compound in water in a water system, the method comprising:
   inducing the halogenated triazole compound to fluoresce;
   measuring an intensity of fluorescence emitted from the water at a pH in a range of from 5 to 12; and
   adjusting the concentration of the halogenated triazole compound in the water based on the measured intensity.

9. The method according to claim 8, wherein, in the adjusting step, the concentration of the halogenated triazole compound is adjusted to be within a predetermined concentration range.

10. The method according to claim 8, wherein the intensity of fluorescence is continuously measured to monitor the concentration of the halogenated triazole compound in the water.

11. The method according to claim 8, further comprising determining the concentration of the halogenated triazole compound in the water based on the measured intensity.

12. The method according to claim 8, wherein, based on the measurement, additional halogenated triazole compound is added to the water to increase the concentration of the halogenated triazole compound in the water.

13. The method according to claim 11, further comprising:
adding an independent fluorescent tracer into the water in a predetermined ratio with the halogenated triazole compound;
measuring an intensity of fluorescence of the independent fluorescent tracer;
determining the concentration of the independent fluorescent tracer in the water based on the measured intensity; and
correlating the concentration of the fluorescent tracer to the concentration of the halogenated triazole compound to determine the relative consumption of the halogenated triazole compound in the water.

14. The method according to claim 8, wherein the halogenated triazole comprises a triazole selected from the group consisting of benzotriazole, tolyltriazole, mercaptobenzothiazole, butylbenzotriazole, and salts thereof.

15. The method according to claim 7, wherein chlorine is present in the water in an amount in a range of from about 0.1 to about 25 mg/L.

16. The method according to claim 8, wherein chlorine is present in the water in an amount in a range of from about 0.1 to about 25 mg/L.

* * * * *